United States Patent [19]
Glynn

[11] Patent Number: 5,630,791
[45] Date of Patent: May 20, 1997

[54] ORTHOTIC JOINT

[75] Inventor: Daniel W. Glynn, Pembroke, Mass.

[73] Assignee: Glynn Orthopedics Services, Inc., Pembroke, Mass.

[21] Appl. No.: 415,731

[22] Filed: Apr. 3, 1995

[51] Int. Cl.⁶ .................................................. A61F 5/00
[52] U.S. Cl. ........................ 602/16; 602/26; 602/23; 623/44
[58] Field of Search ........................... 602/5, 16, 23, 602/26; 623/27, 43, 44, 46

[56] References Cited

U.S. PATENT DOCUMENTS

| | | | |
|---|---|---|---|
| 1,418,283 | 6/1922 | Cameron | 602/16 |
| 2,632,440 | 3/1953 | Hauser et al. | 602/16 |
| 2,679,650 | 1/1954 | Kleinekathofer | 623/44 |
| 3,172,127 | 3/1965 | Tolotti | 623/44 |
| 3,779,654 | 12/1973 | Horne | 602/16 X |
| 4,353,361 | 10/1982 | Foster | 602/16 |
| 4,409,689 | 10/1983 | Buring et al. | 602/16 X |
| 4,433,679 | 2/1984 | Mauldin et al. | 602/16 |
| 4,463,751 | 8/1984 | Bledsoe | 602/16 |
| 4,655,201 | 4/1987 | Pirmantgen | 602/16 |
| 4,738,252 | 4/1988 | Friddle et al. | 602/16 |
| 4,773,404 | 9/1988 | Townsend | 602/16 |
| 4,817,588 | 4/1989 | Bledsoe | 602/16 |
| 5,005,565 | 4/1991 | Fratesi | 602/16 |
| 5,054,476 | 10/1991 | Petrofsky et al. | 602/16 |
| 5,105,805 | 4/1992 | Lapointe et al. | 602/16 |
| 5,107,824 | 4/1992 | Rogers et al. | 602/16 |
| 5,188,584 | 2/1993 | Petrofsky et al. | 602/16 |
| 5,230,696 | 7/1993 | Silver et al. | 602/16 |
| 5,460,599 | 10/1995 | Davis et al. | 602/16 X |

FOREIGN PATENT DOCUMENTS 2600528  12/1987  France ..................... 602/16

*Primary Examiner*—Linda C. Dvorak
*Attorney, Agent, or Firm*—Hale and Dorr

[57] ABSTRACT

Disclosed is an orthotic joint for an orthotic knee, hip or other similar brace that would eliminate the use of sidebars and would automatically lock upon full extension. The locking mechanism could also be fixed in an unlocked position if desired. Instead of a lock, one of a series of barrels of different diameters could be used as stops. The diameter of the barrel would determine the degree of stop. The locking mechanism or barrel would be vacuum-formed into the knee section of a typical custom-made knee orthosis or knee ankle foot orthosis. A round disk with a range-of-motion cutout and a locking hole is positioned between the thigh and calf portions of the brace. In one embodiment, a plunger mounted through the locking mechanism would roll on a cutout in the disk until reaching the tapered hole and then be forced in by a spring to lock the joint. Barrels, instead of a plunger, could be used if a stop, instead of lock, is desired. The locking mechanism could be unlocked by pulling or turning the plunger. This is accomplisher rotating a machined male part relative to a machined female part.

12 Claims, 7 Drawing Sheets

Figure 5(a)
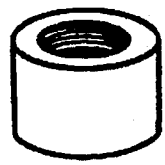
Figure 5(b)
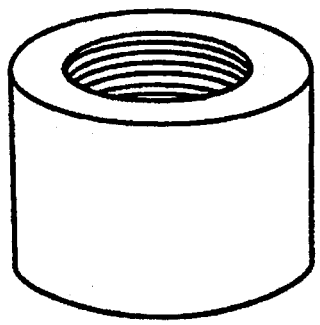
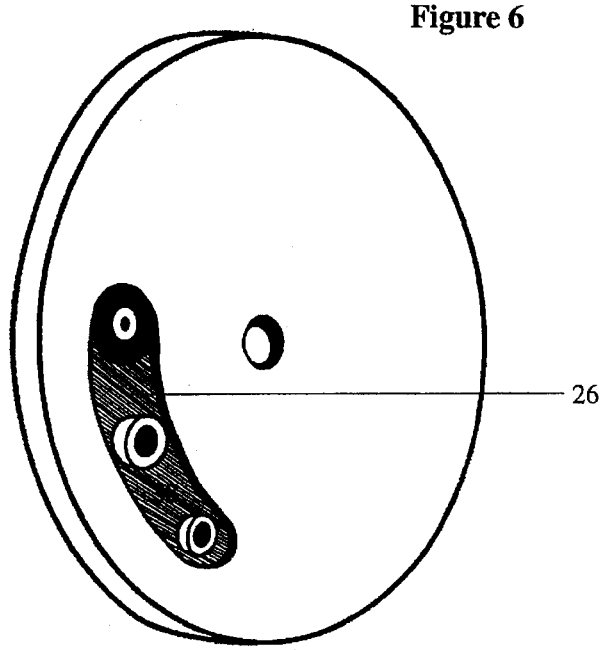
Figure 6
26
Figure 5(c)
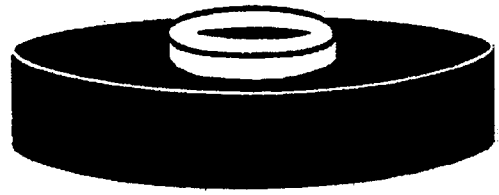

ORTHOTIC JOINT

BACKGROUND OF THE INVENTION

The present invention is related to an orthotic joint, and more particularly to an orthotic plastic joint with a lock or with multiple adjustable extension stops.

Many different types of orthotic knee joints exist. They all have some mechanical joint made to flex and extend with the anatomical knee joints.

Typically, knee joints incorporated into long term knee ankle foot braces (long leg brace) are made of steel with sidebars attached to thigh and calf cuffs. Individuals requiring long term braces generally obtain custom braces made from measurements and a casting of the affected limb. The braces are made by attaching sidebars to a steel joint that flexes and extends in the sagital plane. A drop lock is pushed over the mechanical knee joint to lock the knee joint in place when the leg is fully extended so the knee will not buckle. Steel sidebars are, however, very heavy, and such weight limits the mobility of the brace wearer.

Steel knee joints presently are contoured away from the knee so they will not hit against the leg and cause pressure sores. Sometimes condylar knee pads and straps are added to the knee joints to gain direct control of the knee for medial/lateral correction and stability.

Other orthotic joints are constructed in a similar manner and have many of the same drawbacks. The principles of the invention described below will have application to all such joints.

It is therefore a principal object of the present invention to provide an orthotic joint without sidebars which will automatically lock during full extension.

It is another object of the present invention to provide an orthotic joint without sidebars which has the ability to limit the range of motion of the knee.

Another object of the present invention is to provide an orthotic joint which is lighter and easier to use than existing orthotic joints.

Still another object of the present invention is to provide an orthotic joint that can be vacuum-formed on a positive mold with the attached limb section.

A still further object of the present invention is to provide an orthotic joint which enables the wearer to have greater medial/lateral control.

SUMMARY OF THE INVENTION

The orthotic joint of one embodiment of the present invention will be described as a knee joint and includes one circular disk and a locking mechanism. The disk has a slot cutout which defines the range-of-motion of the leg. A tapered hole is formed at the one end of the slotted cutout. A spring-loaded plunger glides in the range-of-motion cutout. A locking mechanism is attached to the thigh section after it is vacuum-formed. The thigh section is mounted adjacent the disk with the slot cutout. At full extension, a steel plunger would automatically lock into the hole on the slotted disk. It would unlock for sitting with a simple turn or pull. To keep unlocked, the locking mechanism could be rotated an additional distance. Generally, the person using such a brace would want the joint to automatically lock, but, the option to be able to lock in an unlocked mode is available and could prove important to some clients. For instance, a paraplegic that needed a locked knee initially, but, through extensive physical therapy, wanted to test the ability of his quadriceps to lock his knee without the automatic locking mechanism, would be able to do so.

In another embodiment of the present invention a stop mechanism is used instead of the locking mechanism. In this embodiment, a steel barrel of the correct diameter could be used. It would also be attached in the same general area of the thigh section as the automatic locking mechanism. Different range-of-motion stops of different diameters would be used depending on the desired degree of stop required.

These and other features and objects, will become apparent to those skilled in the art from the following detailed description which should be read in a light of the accompanying drawings in which corresponding reference numbers refer to corresponding parts throughout the several views.

BRIEF DESCRIPTION OF THE DRAWINGS

FIGS. 5(a)-5(c) are perspective views of barrels used in the slot of the disk shown in FIG. 4.

FIG. 6 is a perspective view of the disk shown in FIG. 4 with barrels mounted in a slot (although in practice only one barrel would be needed).

DETAILED DESCRIPTION OF THE PREFERRED EMBODIMENT

Figure 1:
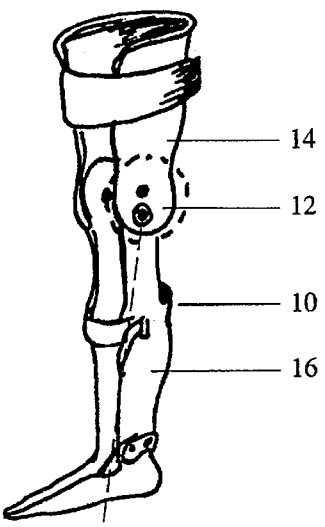
FIG. 1 is a perspective view of an orthotic knee brace of the present invention.
Figure 2:
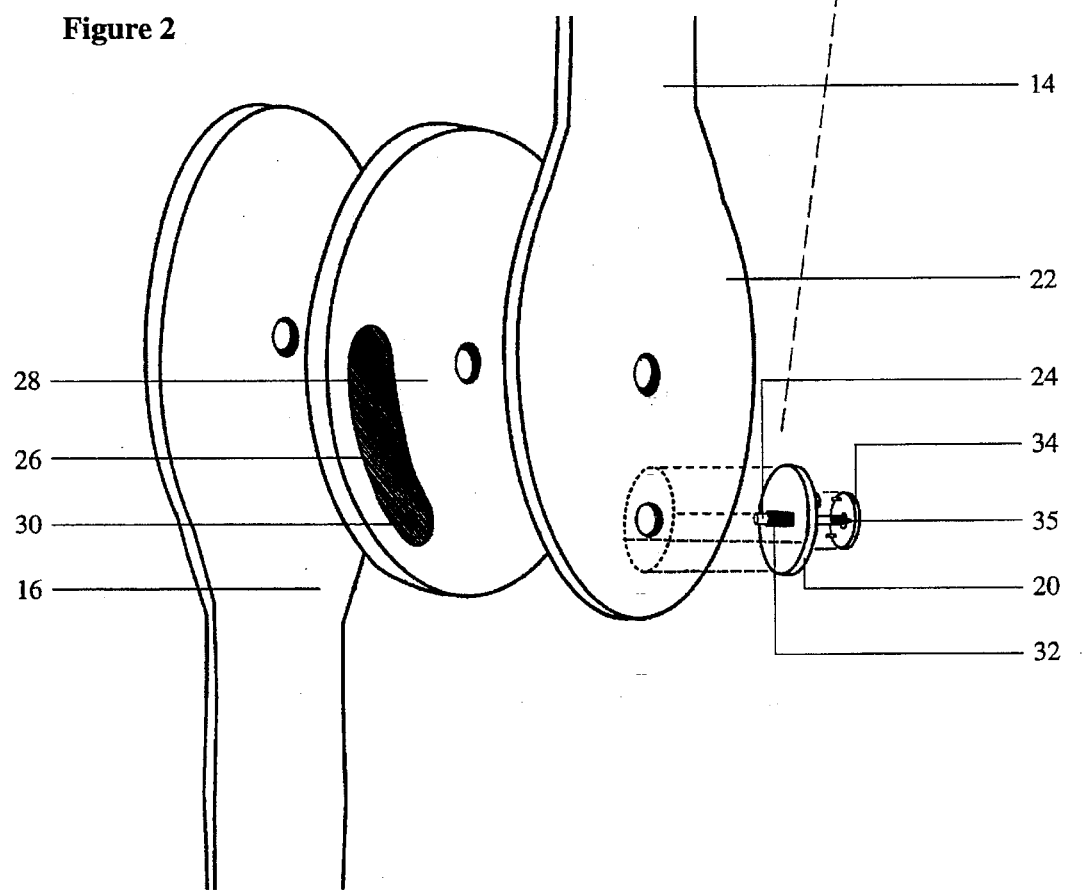
FIG. 2 is an exploded view of the components of the orthotic brace shown in FIG. 1.
Figure 3:
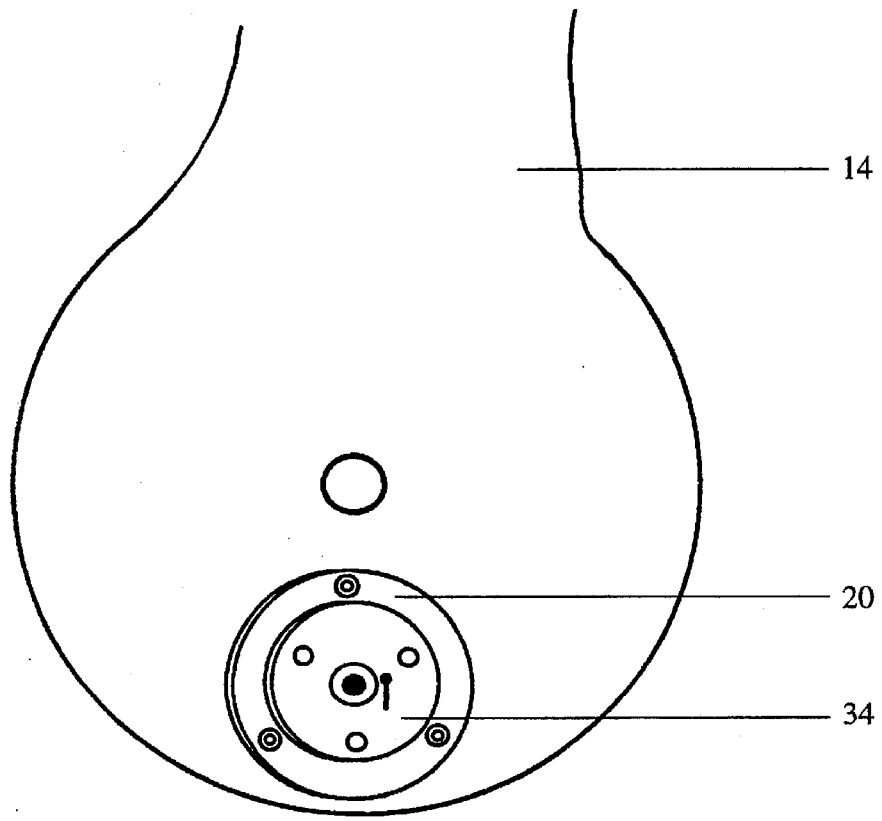
FIG. 3 is a top plan view of the locking mechanism of the present invention mounted on a portion of a leg brace.
Figure 4:
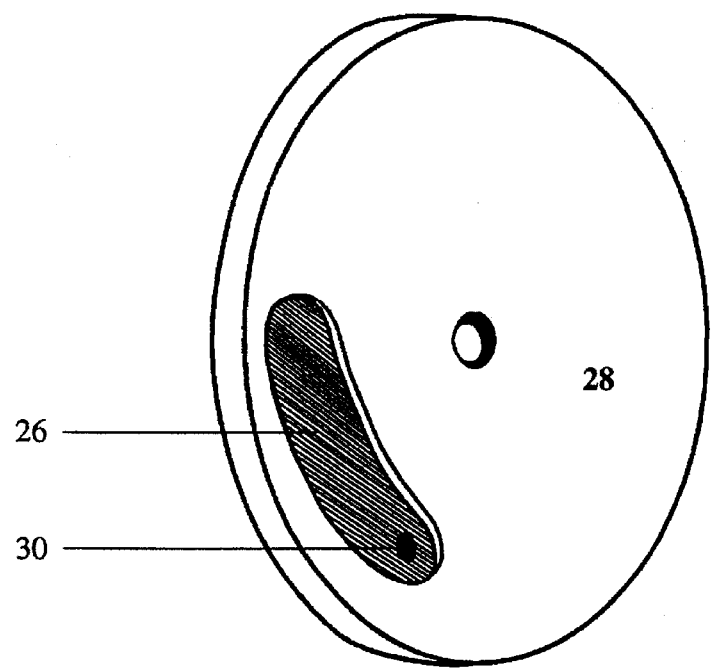
FIG. 4 is a perspective view of a disk mounted between the brace sections shown in FIG. 2.
Figure 19:
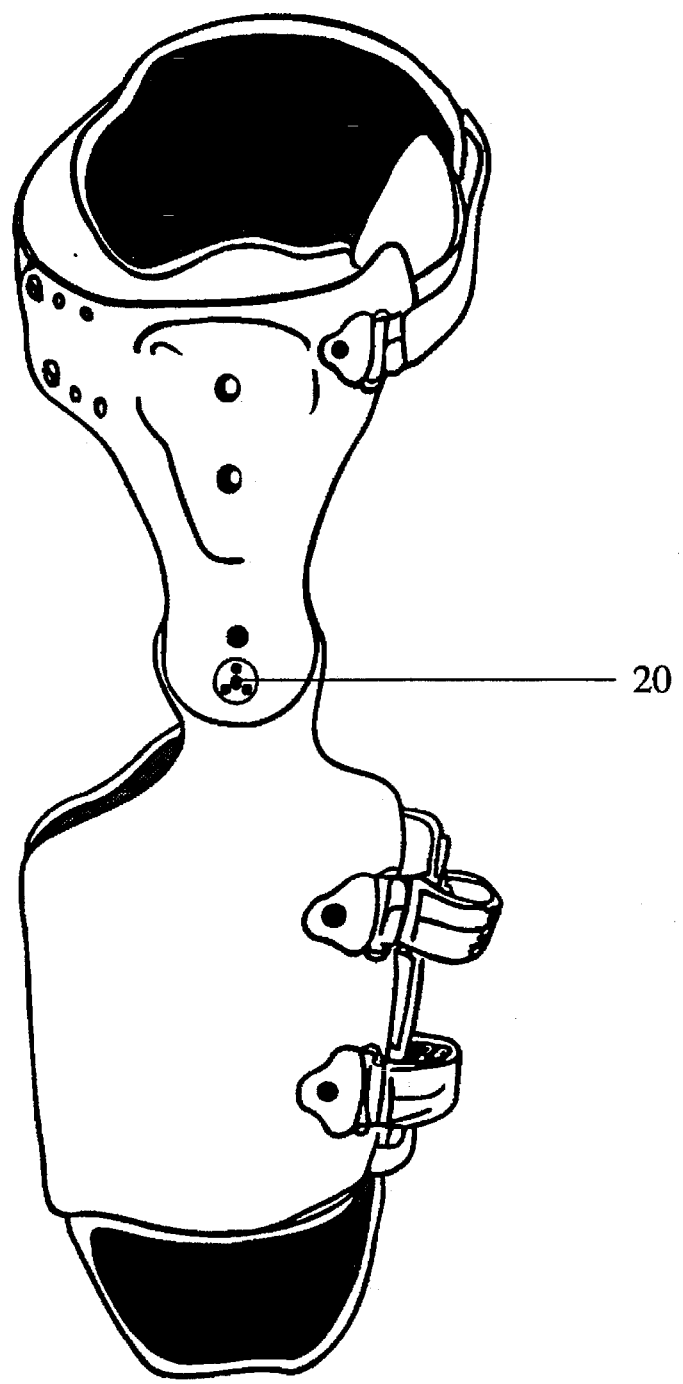
FIG. 19 is a perspective view of a hip orthosis utilizing the locking mechanism shown in FIG. 3.

Referring FIGS. 1 and 2, one embodiment of an orthotic brace 10 of the present invention is shown. The brace 10 shown is a knee brace which includes a knee joint 12. While a knee brace will be described below the present invention could be incorporated in any orthotic joint such as the hip orthosis shown in FIG. 19.

An automatic locking mechanism 20, which can lock the knee joint 12 and thereby lock the calf section 16 relative to the thigh section 14, is mounted on one of the calf or thigh sections 16, 14. In the embodiment shown, it is mounted on the outer wall 22 of the thigh section 14. Locking mechanism 20 has a round stock spring loaded plunger 24 that glides on the range-of-motion cutout 26 in a disk 28 securely mounted (e.g. with screws or rivets) to calf section 14 between thigh and calf sections 14, 16. As thigh section 14 is rotated relative to disk 28, the plunger 24 will glide in cutout 26 until it plunges into the tapered hole 30 on the disk 28. The automatic locking is achieved through the force of the spring 32.

Figure 7:
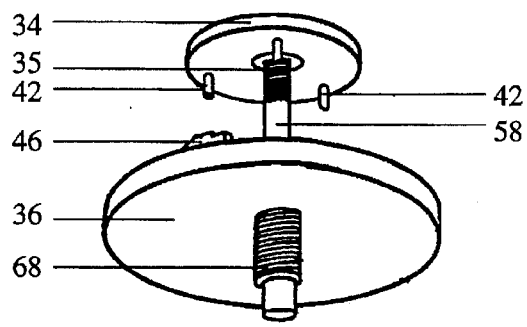
FIG. 7 is a perspective view of one embodiment of the spring-loaded locking mechanism of the present invention shown in FIG. 2.
Figure 8:
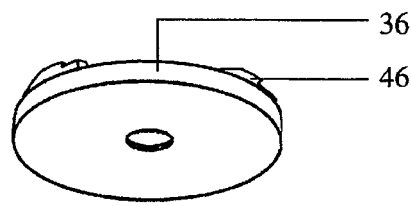
FIG. 8 is a perspective view of the female receptor part of the spring-loaded mechanism shown in FIG. 7.
Figure 10:
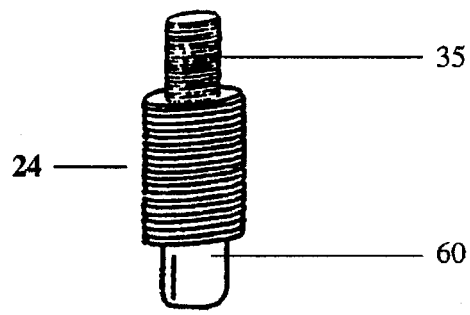
FIG. 10 is a perspective view of the plunger incorporated in the locking mechanism shown in FIG. 7 shown in a compacted position.
Figure 11:
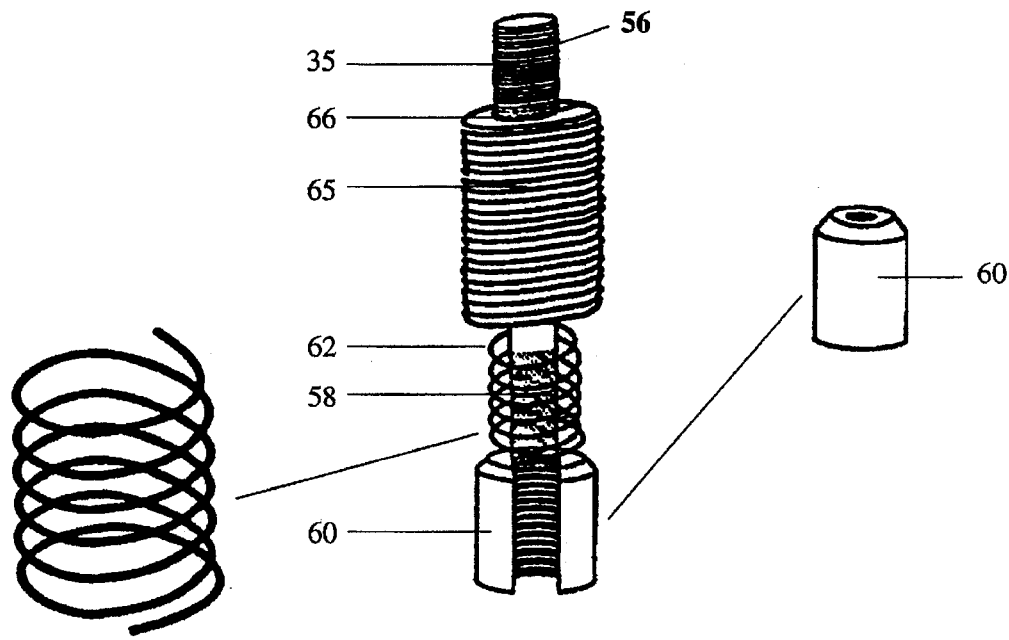
FIG. 11 is an exploded view of the plunger shown in FIG. 10.

In one embodiment shown in FIGS. 7 and 10–11, the plunger 24 includes a top section 56 with threads 35 which screw into the male part 34, and a mid-shaft 58 which is screwed into a bottom section 60. A compression spring 62 is mounted around the mid-shaft 58. A second threaded shaft or encasement 65 is also mounted around mid-shaft 58 so that it glides up and down along mid-shaft 58. The outside diameter of the spring is the same as the outside diameter of the bottom section 60 of the plunger, slightly larger than the outside diameter of the top section 56 and less than the interior diameter of the shaft 65 so that when the plunger 24 is compressed the spring 62 fits within shaft 65. These dimensions ensure that the spring is secured on the mid-shaft 58 between the top of shaft 65 and the bottom section 60. The encasement 64 is threaded into female part 36. The encasement 64 has a tapered hole. The diameter of the tapered hole 66 at the end of the encasement is large enough to allow the top section 56 of the plunger 24 to fit through the hole. The plunger 24 is put under compression by the spring not being able to continue through the hole in the encasement and since the top section 56 of the plunger 24 is screwed to the male part 34 spring tension is increased. The thread 35 in the top section 56 allows for small adjustments for variances in plastic thickness on the vacuum form poles of the fabrication.

While the bottom section 60 of the plunger is unlocked and travelling within the range of motion disk 28 it is under compression until it is forced into the locking hole. At that point, the plunger is still under compression, but the compression is not as great because the plunger has extended approximately 3/16 inches into the locking hole. The travel length is equal to the height of the plateau 52 on the female part 36 which locks the knee joint in an unlocked position. The plunger bottom section 60 which passes into hole 30 can travel no further than the male displacement pins 42 travel because they are stopped at the surface of the female part 36.

Figure 9:
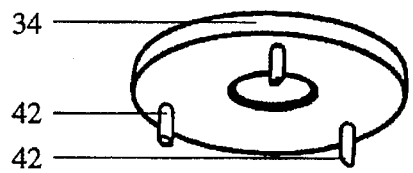
FIG. 9 is a perspective view of the moveable male part of the spring-loaded locking mechanism shown in FIG. 7.
Figure 13:
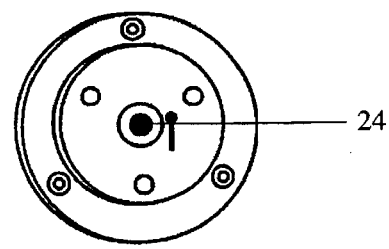
FIG. 13 is a top plan view of the moveable male part shown in FIG. 9 mounted over the stationary female part shown in FIG. 12.

As shown most clearly in FIGS. 7, 9 and 13, male part 34 also includes a set of three displacement pins 42 which extend from one surface of the male part 34. In preferred embodiment, these pins are spaced 120° apart around the male part 34. The purpose of the pins is to keep the male parts 34 separated from the female part 36 when the tension of the spring causes the two parts to come together.

Figure 12:
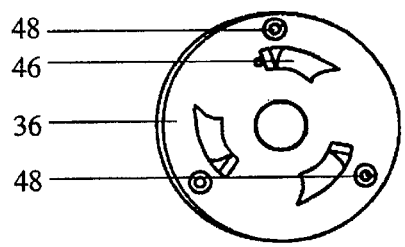
FIG. 12 is a top plan view of the stationary female part shown in FIG. 8.
Figure 14:
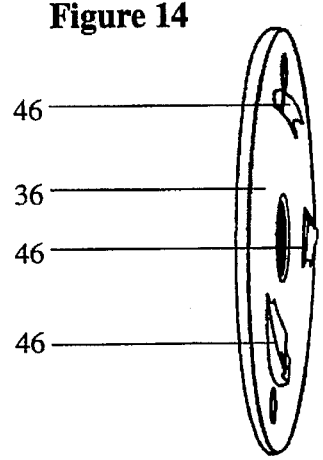
FIG. 14 is another perspective view of the stationary female part shown in FIG. 8.
Figure 15:
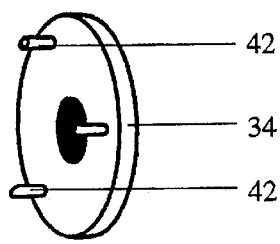
FIG. 15 is another perspective view of the moveable male part shown in FIG. 9.
Figure 16:
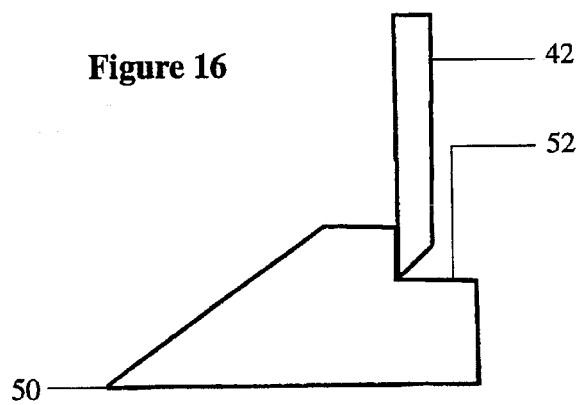
FIGS. 16 and 17 are representative views of the interaction of the displacement pins of the male part shown in FIG. 13 and the ramps on the stationary female part shown in FIG. 12.

When the plunger 24 is not in the tapered hole 30, the male 34 and female 36 parts are separated and the locking mechanism is unlocked. The spring 32 puts the moveable male part 34 under tension to be drawn close to female part 36. As shown in FIGS. 12 and 14, the female part 36 also includes three ramps 46 which are formed on a surface of the female part 36. These ramps are preferably spaced apart 120° from each other. In any event, the ramps 46 are spaced apart the same distance as the displacement pins 42 are spaced from each other. The ramps 46 should be located the same distance from the center hole of the female part 36 as each corresponding pin 42 is located from the center hole of the male part 34.

When locking mechanism 20 locks, the male 34 and female 36 parts come together and contact each other in three locations 120 degrees apart. To unlock the knee joint for sitting, the wearer of the brace either pulls or turns the moveable male part 34. Since the plunger 24 is threaded into the male part 34, the plunger 24 moves with the male part 34 and comes out of the tapered hole 30. Turning the male part 34 causes its set of displacement pins 42 to slide up the ramps 44 formed on the female stationary part 36 thereby causing the plunger 24 to come out of hole 30. Since the female part 36 is stationary, it is preferably attached to the outer disk portion of calf section 16 by any known fabricating means, and in one embodiment it is attached with three small screws 48 which are spaced apart by 120 degrees. These screw holes could also be placed on stationary female part 36 between ramps 46 if a smaller diameter, lower profile female part 36 is desired.

Figure 17:
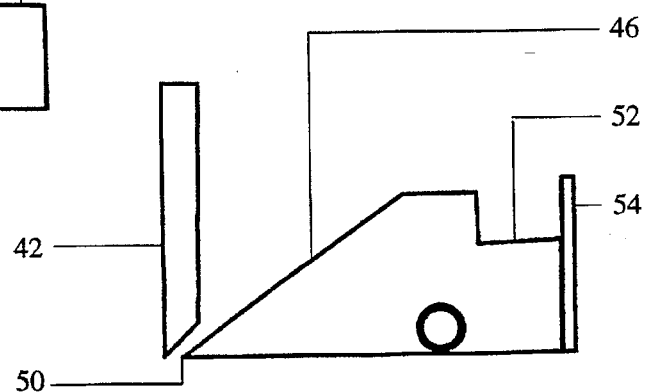

A slight turn of the male part 34 unlocks the knee joint for sitting. The act of pulling and turning the male part 34 and starting to flex the knee is enough to move the plunger 24 out of the tapered hole 30. Once the slight turn or pull is stopped, the plunger 24 is put back under pressure as the male displacement pins 40 slide closer to the female receptor site base 50. The nature of the spring's recoil properties wants to pull male part 34 back towards the female part 36 as shown in FIG. 17. The action of the spring's recoil properties puts the plunger 24 under tension ready to "pop" back into the tapered hole 30 upon leg extension.

To lock the locking mechanism 20 in an unlocked mode, the male part 34 would be turned an additional distance. This would cause the displacement pins 42 to slide further up the ramps 46 and drop down slightly to fix on a plateau 52 on the female part 36 that is half the height of female ramp 46 incline. The male part 34 is then fixed on plateau 52 which is high enough to raise the plunger 24 out of the tapered hole 30. A safety dowel 54 is positioned in a preferred embodiment against only one of the three ramps 46 to prevent overturning of the male part 34 when locking in an unlocked mode.

Since brace wearers either need to have their joint (knee, ankle, hip, etc.) locked or unlocked, the feature enabling locking in an unlocked position is an enhancement for testing clients with or without their joint locked. Once the position is decided, the plunger 24 could be put in the optimum position and kept there.

If locking is never desired, then the locking mechanism 20 can be replaced by a round barrel 58(a), 58(b), or 58(c) mounted on the brace to fit in the cutout 26. The round barrel 58(a), 58(b) or 58(c) would simply be used to limit the range of motion of the joint. The diameter of the barrel 58(a), 58(b), or 58(c) would determine where the joint was stopped when extended. Three barrels 58(a)–58(c) of different diameter are shown together in the range-of-motion cutout 26 for comparison. Only one barrel would be used at a time depending on the degree stop desired. The larger the diameter, the larger the degree of stop because the barrel edge 20 would hit the edge of the range-of-motion cutout 26 sooner when the leg extends.

The same disk 28 can be used with locking mechanism 20 or barrels 58(a)–58(c). The barrels are attached to the inner surface of the disk portion of thigh section 14. The stopping screw and barrel 58(a), 58(b) or 58(c) attaches in the same place as the locking mechanism 20. Either the stopping barrel 58(a), 58(b) or 58(c) or the locking mechanism 20 would be used, and they would not be used at the same time.

Figure 18:
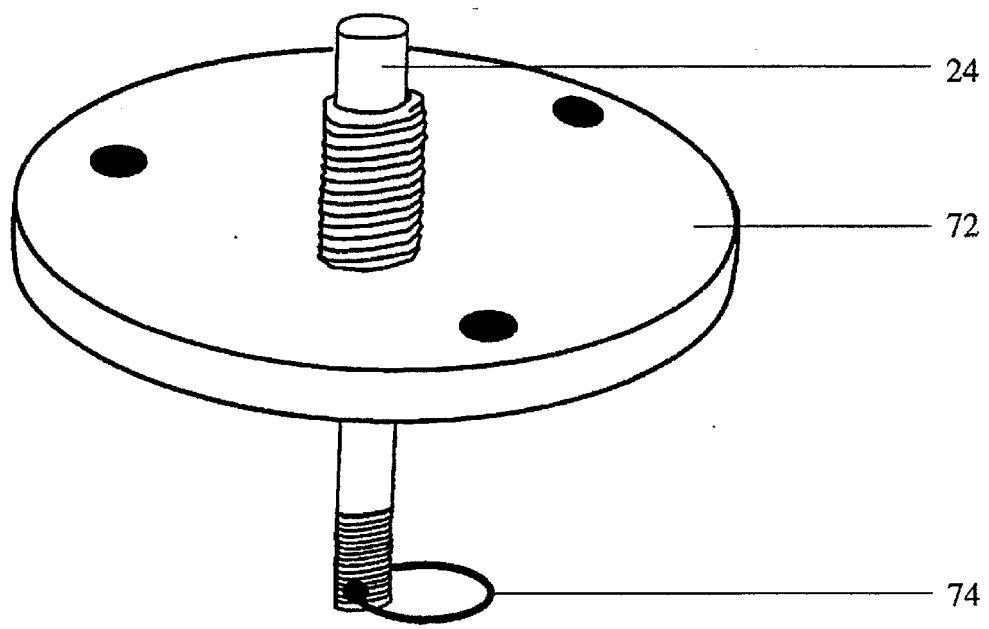
FIG. 18 is a perspective view of an alternate embodiment of the locking mechanism of the present invention.

Turning now to FIG. 18, an alternate embodiment of the present invention is shown which utilizes the plunger shown in FIGS. 10 and 11 and a stationary female part 72 which is mounted to an orthotic joint in the same manner as female part 36. This locking mechanism is engaged simply by pulling on ring 74 to pull the plunger 24 out of engagement with hole 30 and cutout 26.

The joint described above is intended for use in any long-term orthotic joint candidates. The joint should be incorporated into a typical custom-made vacuum-formed brace such as the hip orthosis shown in FIG. 19. Because of its light weight, a brace incorporating this joint would not require the use of aluminum and/or steel sidebars or steel joints. As a result, the brace would be considerably lighter which would make it useful not only with the elderly but with children as well. Although in the preferred embodiment, the various components are manufactured through polypropylene vacuum-forming, the brace could also formed using composite resin which would make it a stronger brace.

Orthotic joints are also preferably marketed in kits and sold to orthotic practitioners who have the ability to vacuum-form their own orthoses. The kits would preferably contain a one-quarter inch thick plastic disk 28 approximately two and three-eighths inches in diameter. The one quarter inch thick disk 28 would have a range-of-motion cutout 26 which would be approximately one-eighth inch deep. The knee locking mechanism 20 would also be pre-assembled in the kit. If barrels 58(a)–58(c) were used instead of the locking mechanism 20, the one-quarter inch plastic disk 28 would also still be used. There also could be an adaptable extension lever that could be sold with the locked knee kit for the physically challenged that could not reach down to unlock the knee. This would be an extension fulcrum lever.

While the foregoing invention has been described with reference to its preferred embodiments, various alterations and modifications will become apparent to one skilled in the art. All such alterations and modifications are intended to fall within the scope of the appended claims.

What is claimed is:

1. An orthotic brace comprising:

a first molded support member and a second molded support member, said first and second support members being shaped so that when mated at adjacent ends said first and second support members rotate about a common axis;

a disk positioned between said mating portions of said adjacent ends of said first and second support members, said disk including an arc-shaped cutout on one surface of said disk, said cutout extending only partially through the depth of said disk;

means mounted to one of said first and second support members for passing into said cutout to limit the range of motion of said first support member relative to said second support member.

2. The orthotic brace of claim 1 wherein said means mounted to one of said first and second support members is a locking mechanism comprising:

a female part having an opening therethrough;

a male part to which a spring-loaded plunger is connected, said spring-loaded plunger having one end with dimensions small enough to allow said one end to pass through said opening through said female part.

3. The orthotic brace of claim 2 further comprising means for keeping said male and female members separated from each other.

4. The orthotic brace of claim 3 wherein said means for keeping said male and female members separated from each other comprises displacement pins mounted on a surface of one of said male and female members.

5. The orthotic brace of claim 3 wherein said means for keeping said male and female members separated from each other comprises ramps extending from a surface of one of said male and female members.

6. The orthotic brace of claim 4 further comprising ramps extending from a surface of one of said male and female members.

7. The orthotic brace of claim 2 wherein said spring-loaded plunger is a compression spring plunger.

8. The orthotic brace of claim 2 wherein said spring-loaded plunger is a torque spring plunger.

9. The orthotic brace of claim 2 further comprising means for locking said locking mechanism in an unlocked position.

10. The orthotic brace of claim 9 wherein said means for locking said locking mechanism in an unlocked position comprises a second surface positioned above a surface of said male or female part to which it is attached.

11. The orthotic brace of claim 1 wherein said means to limit the range of motion has dimensions small enough to allow it to fit within said arc-shaped cutout.

12. The orthotic brace of claim 11 wherein said range of motion limiting means is a barrel mounted on one of said molded first and second support sections so that when said disk with said arc-shaped cutout is positioned adjacent said barrel said barrel fits within at least a portion of said arc-shaped cutout.

* * * * *